(12) United States Patent
Pittman et al.

(10) Patent No.: US 9,827,386 B2
(45) Date of Patent: Nov. 28, 2017

(54) SYSTEM AND METHOD FOR CONTROLLING LEAKAGE OF A CIRCUIT DELIVERING A PRESSURIZED FLOW OF BREATHABLE GAS TO A SUBJECT

(75) Inventors: Stephen Dalton Pittman, Brookline, MA (US); Lauren Elizabeth Hueser, Brighton, MA (US)

(73) Assignee: Koninklijke Philips N.V., Eindhoven (NL)

( * ) Notice: Subject to any disclaimer, the term of this patent is extended or adjusted under 35 U.S.C. 154(b) by 897 days.

(21) Appl. No.: 13/318,705

(22) PCT Filed: May 11, 2010

(86) PCT No.: PCT/IB2010/052089
§ 371 (c)(1),
(2), (4) Date: Nov. 3, 2011

(87) PCT Pub. No.: WO2010/140072
PCT Pub. Date: Dec. 9, 2010

(65) Prior Publication Data
US 2012/0060839 A1    Mar. 15, 2012

Related U.S. Application Data

(60) Provisional application No. 61/183,622, filed on Jun. 3, 2009.

(51) Int. Cl.
*A61M 16/00* (2006.01)
*A61M 16/20* (2006.01)

(52) U.S. Cl.
CPC .......... *A61M 16/00* (2013.01); *A61M 16/202* (2014.02); *A61M 16/203* (2014.02); *A61M 2205/15* (2013.01); *A61M 2205/3331* (2013.01); *A61M 2205/50* (2013.01)

(58) Field of Classification Search
CPC .............. A61M 16/00; A61M 16/0051; A61M 2016/0039; A61M 2016/0021; A61M 16/06; A61M 11/06; A61F 5/08
USPC ............ 128/200.24, 202.22, 203.12, 203.14, 128/204.18, 204.21–204.23, 205.23, 128/205.24, 203.25
See application file for complete search history.

(56) References Cited

U.S. PATENT DOCUMENTS

| | | | |
|---|---|---|---|
| 3,903,881 A * | 9/1975 | Weigl | 128/204.25 |
| 6,041,780 A * | 3/2000 | Richard | A61M 16/00 128/204.18 |
| 6,626,175 B2 | 9/2003 | Jafari et al. | |
| 2005/0016536 A1 | 1/2005 | Rapoport et al. | |
| 2005/0056284 A1 | 3/2005 | Rascoe et al. | |
| 2006/0000475 A1 | 1/2006 | Matthews et al. | |
| 2007/0028920 A1 | 2/2007 | Acker et al. | |

FOREIGN PATENT DOCUMENTS

| | | |
|---|---|---|
| CN | 101299963 A | 11/2008 |
| JP | 00819608 A | 1/1996 |
| JP | 2005103311 A | 4/2005 |
| WO | 9639206 A2 | 12/1996 |

* cited by examiner

*Primary Examiner* — Todd J Scherbel
*Assistant Examiner* — Ned T Heffner

(57) ABSTRACT

A pressurized flow of breathable gas is delivered to the airway of a subject through a gas circuit (16) as part of a therapy regime. Leakage of gas from within the circuit to atmosphere to prevent re-breathing of gas is dynamically adjusted to stabalize the total amount of leakage.

9 Claims, 2 Drawing Sheets

SYSTEM AND METHOD FOR CONTROLLING LEAKAGE OF A CIRCUIT DELIVERING A PRESSURIZED FLOW OF BREATHABLE GAS TO A SUBJECT

The invention relates to delivering a pressurized flow of breathable gas to a subject through a circuit while dynamically controlling gas leakage from inside the circuit to atmosphere.

Systems configured to deliver a pressurized flow of breathable gas to the airway of a self-ventilating subject for therapeutic purposes are known. For example, positive airway pressure systems are commonly used to provide pressurized airway support to subjects during sleep to reduce the symptoms of sleep disordered breathing. These systems deliver the pressurized flow of breathable gas through a circuit that often includes a mechanism for leaking gas to atmosphere to prevent re-breathing. However, these mechanisms are generally fixed structurally, and leak gas from within the circuit in a static manner.

One aspect of the invention relates to a system configured to deliver a pressurized flow of breathable gas to the airway of a subject. In one embodiment, the system comprises a gas circuit, a valve, one or more sensors, and a processor. The gas circuit forms an inlet, an outlet, and a lumen that places the inlet in communication with the outlet. The outlet is configured to deliver the pressurized flow of breathable gas to the airway of a subject. The valve is configured to release gas inside the circuit to atmosphere. The one or more sensors are configured to generate one or more output signals that convey information related to one or more gas parameters within the gas circuit related to gas leakage from within the circuit to atmosphere. The processor is configured to control the valve such that the amount of gas released from inside the circuit to atmosphere is based on the one or more output signal generated by the one or more sensors.

Another aspect of the invention relates to a method of delivering a pressurized flow of breathable gas to the airway of a subject. In one embodiment, the method comprises delivering a pressurized flow of breathable gas to the airway of a subject through a circuit that interfaces with the airway of the subject; generating one or more output signals that convey information related to one or more gas parameters of the pressurized flow of breathable gas related to leakage of gas in the pressurized flow of breathable gas from within the circuit to atmosphere; and releasing gas within the circuit to atmosphere at a controlled rate based on the one or more output signal generated by the one or more sensors.

Another aspect of the invention relates to a system configured to deliver a pressurized flow of breathable gas to the airway of a subject. In one embodiment, the system comprises means for delivering a pressurized flow of breathable gas to the airway of a subject, wherein the means for delivering interfaces with the airway of the subject; means for generating one or more output signals that convey information related to one or more gas parameters of the pressurized flow of breathable gas related to leakage of gas in the pressurized flow of breathable gas from within the means for delivering to atmosphere; and means for releasing gas within the means for delivering to atmosphere at a controlled rate based on the one or more output signal generated by the means for generating.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 3:
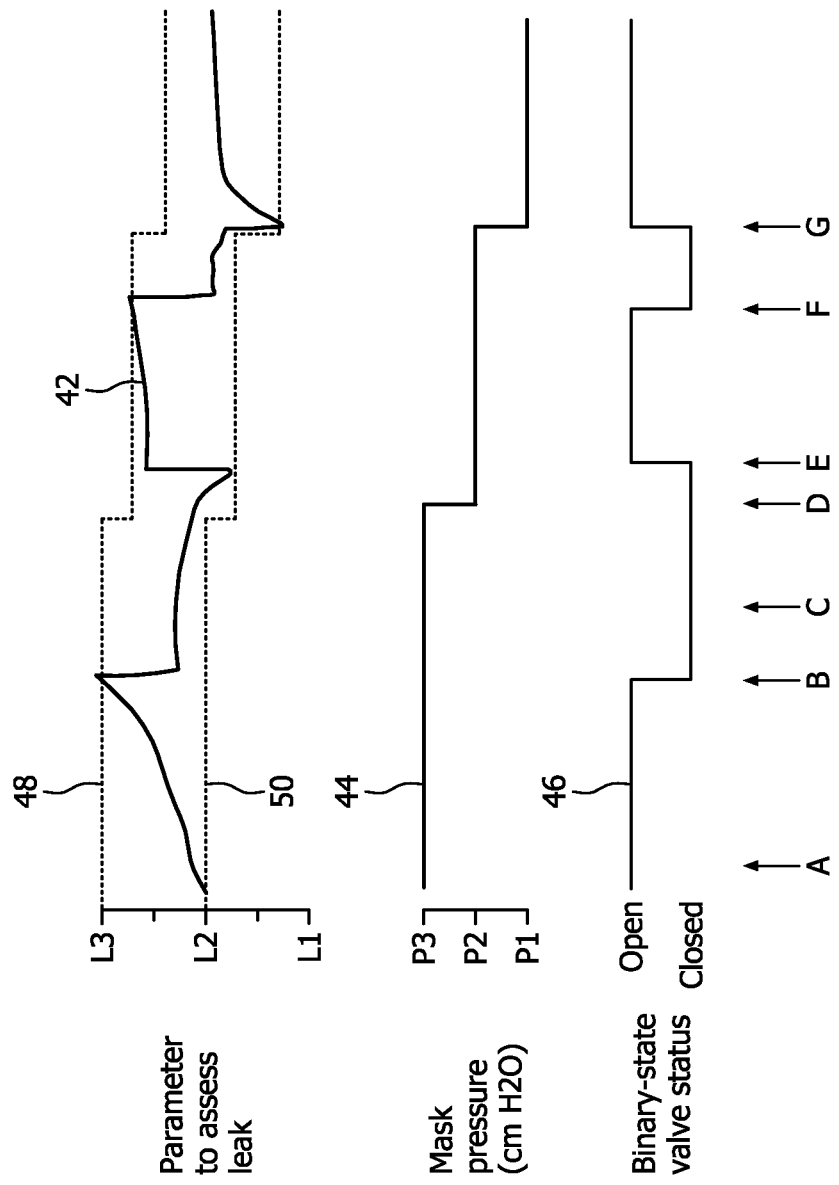

FIG. 3 includes plots of a parameter related to leakage, pressure within an interface appliance, and a mode of operation of a valve, in accordance with one or more embodiments of the invention.

Figure 1:
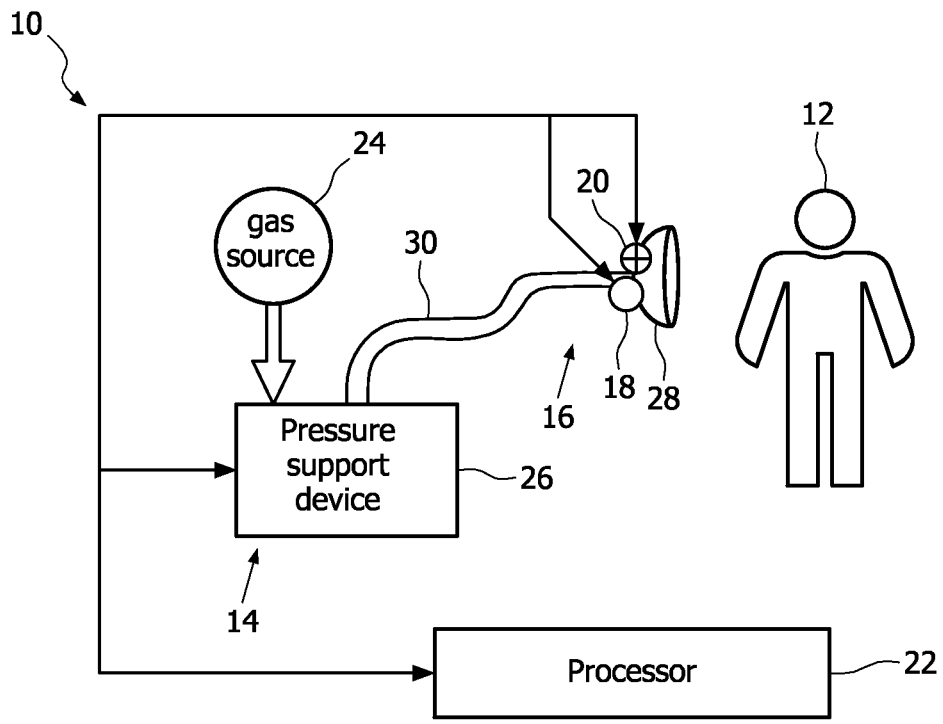
FIG. 1 illustrates a system configured to deliver a pressurized flow of breathable gas to the airway of a subject, in accordance with one or more embodiments of the invention.

FIG. 1 illustrates a system 10 configured to deliver a pressurized flow of breathable gas to the airway of a subject 12. In particular, system 10 is configured to deliver the pressurized flow of breathable gas to the airway of subject 12 as part of a therapy regime. In delivering the pressurized flow of breathable gas to the airway of subject 12, system 10 adaptively and/or dynamically adjusts the amount of gas that is leaked to atmosphere in order to prevent re-breathing of gas by 12 based on the amount of gas that is leaked to atmosphere "unintentionally." In one embodiment, system 10 includes a pressure generator 14, a circuit 16, one or more sensors 18, one or more valves 20, and a processor 22.

Pressure generator 14 is configured to generate a pressurized flow of breathable gas for delivery to the airway of subject 12 by circuit 16. One or more parameters of the pressurized flow of breathable gas generated by pressure generator 14 may be controlled in accordance with the parameters of a therapy regime. The therapy regime may include, for example, a pressure therapy algorithm designed to provide positive airway pressure support to a self-ventilating subject 12 during bedtime. This positive airway pressure support provided to subject 12 will provide therapeutic benefits to subject 12 that reduce the symptoms of sleep disordered breathing experienced by subject 12. The pressure therapy algorithm may include one or more of a bi-PAP algorithm, a CPAP algorithm, auto-titrating CPAP, servo-ventilation, backup breaths, comfort features such as C-Flex, reducing pressure during early expiration, and/or other pressure therapy algorithms. The one or more parameters of the pressurized flow of breathable gas controlled in accordance with the therapy regime may include one or more of a pressure, a flow rate, a composition, a volume, a temperature, a humidity, and/or other parameters of the pressurized flow of breathable gas. In one embodiment, pressure generator 14 includes a gas source 24 and a pressure support device 26.

Gas source 24 includes a body or bodies of gas from which pressure support device 26 generates the pressurized flow of breathable gas that is delivered to subject 12. Gas source 24 may include any supply of breathing gas, such as, for example, ambient atmosphere, a tank of pressurized gas, a wall gas source, and/or other bodies of breathable gas. The breathing gas from gas source 24 can be any breathable gas, such as air, oxygen, an oxygen mixture, a mixture of a breathing gas and a medication, which can be in gaseous form (e.g., nitric oxide, nebulized, etc.), and/or other breathable gases.

Pressure support device 26 includes one or more mechanisms for controlling one or more parameters of the flow of breathable gas released from pressure support device 26 to circuit 16 (e.g., pressure, flow, etc.). For example, pressure support device 26 may include one or more of a valve, a blower, a piston, a bellows, and/or other mechanisms for controlling one or more parameters of the flow of breathable gas. The pressure support device 26 may include a positive airway pressure support device configured to generate the pressurized flow of breathable gas for delivery to subject 12 in accordance with a therapy regime designed to reduce the symptoms of sleep disordered breathing experienced by subject 12 during sleep.

Circuit 16 defines a gas flow path between pressure generator 14 and the airway of subject 12. As such, circuit 16 is configured to deliver the pressurized flow of gas from pressure generator 14 to the airway of subject 12. In one embodiment, circuit 16 includes one or more of an interface appliance 28 and a conduit 30.

Interface appliance 28 is configured to communicate gas between the airway of subject 12 and circuit 16. Interface appliance 28 may include either an invasive or non-invasive appliance for communicating gas between circuit 16 and the airway of subject 12. For example, interface appliance 28 may include a nasal mask, nasal/oral mask, total face mask, nasal cannula, endotracheal tube, LMA, tracheal tube, and/or other interface appliance.

Conduit 30 forms a lumen between an inlet of circuit 16 that connects with pressure support device 18 and an outlet of circuit 16 formed by interface appliance 28. In one embodiment, conduit 30 is flexible. Conduit 30 may be formed integrally with interface appliance 28. Or, conduit 30 may be formed separately from interface appliance 28. In one embodiment in which conduit 30 and interface appliance 28 are formed separately, conduit 30 and interface appliance 28 are selectably detachable.

Although circuit 16 is illustrated in FIG. 1 as a single-limbed circuit for communicating a pressurized flow of breathable gas with the airway of subject 12, this is not intended to be limiting. In one embodiment circuit 16 is a double-limbed circuit with a separate portion (e.g., a separate limb of conduit 30) configured to convey gas away from the airway of subject 12.

Generally, the interface between interface appliance 28 and the airway of subject 12 is not perfect. For example, if interface appliance 28 includes a mask that fits over the nose and/or mouth of subject 12, the seal between the mask and the face of subject 12 may not be perfect, and may allow some of the gas within the mask to be leaked to ambient atmosphere. These types of leaks between the interface of interface appliance 28 and the airway of subject 12 are common in other types of interface appliances as well. Similarly, in one embodiment, circuit 16 also includes other sources of leakage from within circuit 16 to atmosphere. For instance, at the connection between interface appliance 28 and conduit 30 and/or at the connection between conduit 30 and pressure support device 26 gas may be leaked to atmosphere. Further, interface appliance 28 and/or conduit 30 may have leaks that permit gas within circuit 16 to be leaked to ambient atmosphere. These leaks may be purposely formed within interface appliance 28 and/or conduit 30 and/or formed in interface appliance 28 and/or conduit 30 through use (e.g., typical wear and tear).

The leakage of gas within circuit 16 to atmosphere during delivery of the pressurized flow of breathable gas to subject 12 may provide benefits within system 10. During use as circuit 16 delivers the pressurized flow of breathable gas to the airway of subject 12 expiration by subject 12 is forced back into circuit 16. This introduction of expired gas into circuit 16 tends to increase the pressure within circuit 16, and to increase the carbon dioxide content of the gas within circuit 16. If some of the expiration gas introduced into circuit 16 during tidal breathing is not leaked from circuit 16 to atmosphere, then subject 12 may not receive sufficient oxygen from the pressurized flow of breathable gas due to re-breathing.

Although leakage of at least some of the gas within circuit 16 to atmosphere is somewhat beneficial within system 10 (particularly leakage of the gas close to the interface between subject 12 and circuit 16 that is more likely to be higher in carbon dioxide content), excessive leakage may reduce the comfort, effectiveness, efficiency, and/or convenience of treatment provided to subject 12 by system 10. For example, excessive leak from within circuit 16 to atmosphere may increase the amount of audible noise generated by system 10, compromise pressure regulation within circuit 16, compromise the detection of respiratory events based on gas parameters within circuit 16 (e.g., by a processor associated with pressure generator 14), increase the load on pressure generator 14 required to maintain the appropriate pressure within circuit 16, and/or otherwise inhibit the comfort, effectiveness, efficiency, and/or convenience of the treatment provided to subject 12 by system 10.

The sensors 18 are configured to monitor one or more parameters of the pressurized flow of breathable gas delivered to the airway of subject 12. For example, sensors 18 may include one or more sensors configured to generate output signals conveying information related to one or more a pressure, a flow rate, a composition, a volume, a temperature, a humidity, and/or other parameters of the pressurized flow of breathable gas. Such sensors may include, for instance, one or more of a pressure sensor, a flowmeter, a capnometer, and/or other sensors configured to generate output signals conveying information related to one or more parameters of the pressurized flow of breathable gas. The sensors 18 may be disposed in system 10 so as to be in communication with the pressurized flow of breathable gas inside pressure support device 26, inside interface appliance 28, and/or within the lumen formed by conduit 30. For example, one or more of sensors 18 may be disposed in a positive airway pressure support system that includes pressure support device 26, interface appliance 28, and/or conduit 30.

The one or more valves 20 are configured to release gas within circuit 16 to atmosphere. The one or more valves 20 are configured so that the rate at which gas is released from within circuit 16 to atmosphere is controllable. Controlling the rate at which one or more valves 20 release gas from within circuit 16 to atmosphere enables the amount of leak from circuit 16 to atmosphere to be controlled (e.g., as is discussed further below).

In one embodiment, one or more valves 20 include a 2-state binary valve that operates at two modes. At a first mode, the valve releases gas from circuit 16 at a first rate. At a second mode, the valve releases gas from circuit 16 at a second rate. The first mode may be an "open" mode in which gas is permitted to pass relatively freely through an opening formed by the valve. The second mode may be a "closed"

mode in which the opening formed by the valve is effectively shut off such that the second rate is at or near zero.

In one embodiment, the one or more valves 20 include a valve that can be controlled to permit gas to pass through the valve from within circuit 16 to atmosphere at a plurality of rates. To accomplish this, the valve may provide an opening that can be incrementally adjusted in size, a plurality of openings that can be selectively opened or closed individually or in groups to adjust the rate at which gas is released to atmosphere, and/or other mechanisms for adjusting the rate at which gas is released to atmosphere In the embodiment depicted in FIG. 1, one or more valves 20 include a valve disposed on interface appliance 28. This may facilitate the leakage of expiration gas (e.g., having an elevated level of carbon dioxide) to prevent re-breathing. It should be appreciated that this is not intended to be limiting. In one embodiment, one or more valves 20 include a valve disposed on conduit 30. In one embodiment, one or more valves 20 include valves disposed on interface appliance 28 and conduit 30.

Processor 22 is configured to provide information processing capabilities in system 10. As such, processor 2 may include one or more of a digital processor, an analog processor, a digital circuit designed to process information, an analog circuit designed to process information and/or control component(s) within system 10, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device, or processor 22 may represent processing functionality of a plurality of devices operating in coordination. Processor 22 may be configured to provide the functionality described below by executing one or more computer program modules. Processor 22 may be configured to execute the modules by software; hardware; firmware; some combination of software, hardware, and/or firmware; and/or other mechanisms for configuring processing capabilities on processor 22. Processor 22 may include one or more components disposed integrally within, and/or carried on, pressure generator 14, interface appliance 28, and/or conduit 30.

As was discussed above, during delivery of the pressurized flow of breathable gas to subject 12 by system 10, gas from within circuit 16 will be leaked to ambient atmosphere. This may include gas that is intentionally leaked (e.g., to prevent re-breathing), and/or gas that is unintentionally leaked (e.g., due to equipment wear, airway interface leakage, etc.). The processor 22 is configured to control one or more valves 20 to regulate the leakage from within circuit 16 to atmosphere in order to enhance the effectiveness, efficiency, comfort, and/or convenience of the therapy provided to subject 12 by system 10 through the pressurized flow of breathable gas. In particular, processor 22 is configured to stabilize the leakage from within circuit 16 to atmosphere.

In order to stabilize the leakage from within circuit 16 to atmosphere by controlling one or more valves 20, processor 22 bases the control of one or more valves 20 on the one or more output signals generated by sensors 18. More specifically, processor 22 bases the control of valves 20 and output signals generated by sensors 18 that convey information about a gas parameter within circuit 16 related to leakage of gas from circuit 16 to atmosphere. By way of non-limiting example, the gas parameter within circuit 16 upon which control of valves 20 is based may include a flow rate of gas within circuit 16, or an estimated flow rate of the gas within circuit 16 being leaked to atmosphere.

In one embodiment, processor 22 controls valves 20 to gradually decrease the rate at which gas is leaked from within circuit 16 to atmosphere as the output signals generated by sensors 18 indicate that leakage is increasing. For example, the area of the opening(s) of valves 20 through which gas can leak from within circuit 16 to atmosphere may be determined as a function of (e.g., proportional to) the gas parameter related to leak within circuit 16. This type of dynamic adjustment will decrease the amount of gas leaked to atmosphere through valves 20 as the amount of unintentional leakage of the gas within circuit 16 to atmosphere increases, and vice versa.

In some embodiments, valves 20 include a binary 2-state valve that is operable in a first mode and a second mode. If valve 20 is operated in the first mode, valve 20 provides an opening of a first size through which gas within circuit 16 is leaked. If valve 20 is operated in the second mode, valve 20 provides an opening that is smaller than the first opening, or even no opening at all. If valve 20 is configured such that the opening in the second mode is closed or substantially closed, valve 20 is effectively shut off in the second mode.

In these embodiments, processor 22 may control valve 20 such that valve 20 is switched by processor 22 between the first mode and the second mode based on whether the output signals generated by sensors 18 indicate an amount of leakage that breaches one or more thresholds. For example, in one embodiment, the output signals generated by sensors 18 convey information about a first gas parameter related to leakage of gas within circuit 16 to atmosphere. The first gas parameter may include, for instance, flow rate within circuit 16 and/or estimated flow rate of leakage. If the output signals generated by sensors 18 indicate that the first gas parameter has risen above an upper threshold level (e.g., the output signals rise above a corresponding threshold level), processor 22 controls valve 20 to switch from the first mode to the second mode, thereby reducing the amount of leakage.

Once valve 20 has switched to the second mode of operation, processor 22 may eventually control valve 20 to switch back to the first mode of operation. For example, processor 22 may switch valve 20 back to the first mode of operation after a predetermined period of time. As another example, processor 22 may maintain valve 20 in the second mode of operation until the first gas parameter has fallen below a lower threshold level. Once the output signals generated by sensors 18 indicate that the first gas parameter has dropped below the lower threshold level (e.g., the output signals drop below a corresponding threshold level), processor 22 controls valve 20 to switch from the second mode of operation back to the first mode of operation, thereby increasing the rate at which gas is leaked through valve 20 to atmosphere.

In one embodiment, the threshold level(s) for the first gas parameter that are used to control valve 20 include at least one threshold level that is static and fixed. A user may configure this at least one level, or this at least one level may be set at the time of manufacture. In one embodiment, the threshold level(s) for the first gas parameter that are used to control valve 20 include at least one threshold level that is adaptive and dynamic. This at least one threshold level may be determined based on the output signals generated by sensors 18. For example, the output signals generated by sensors 18 may convey information about a second gas parameter of gas within circuit 16, and the at least one threshold level may be determined based on the second gas parameter. The second gas parameter may include, for instance, pressure within circuit 16, pressure within interface appliance 28, pressure within circuit 30, OTHERS, and/or other gas parameters.

Figure 2:
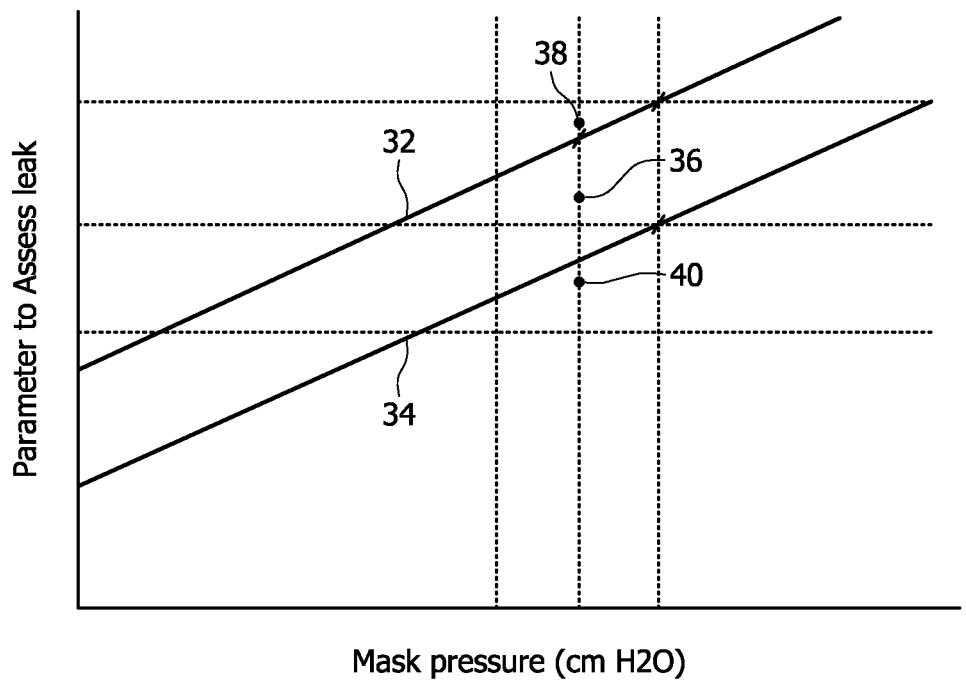
FIG. 2 is a plot of a parameter related to leakage versus pressure within an interface appliance, according to one or more embodiments of the invention.

By way of illustration, FIG. 2 shows a plot of a parameter related to leakage (e.g., the first gas parameter described above) versus pressure within an interface appliance (e.g., interface appliance 28 shown in FIG. 1 and described above). The plot in FIG. 2 includes an upper threshold level 32 for the parameter related to leakage and a lower threshold level 34 for the parameter related to leakage. In the embodiment illustrated in FIG. 2, each of upper threshold level 32 and lower threshold level 34 vary as a function of pressure within the interface appliance.

The plot includes three data points 36, 38, and 40, which illustrate the manner in which a valve that is the same as or similar to valve 20 (shown in FIG. 1 and described above) is controlled in accordance with upper threshold level 32 and lower threshold level 34. Data point 36 is located between upper threshold level 32 and lower threshold level 34. If the parameter related to leakage is at data point 36, the valve will continue to operate in its current mode. For example, if the pressurized flow of breathable gas has been recently commenced with the valve in a default first mode (e.g., the "open" mode described above), the valve will remain in this mode at data point 36.

Data point 38 is above upper threshold level 32. As such, if the parameter related to leakage proceeds from data point 36 to data point 38, the valve will be switched from the first mode of operation into a second mode of operation that reduces or even substantially stops leakage of gas through the valve (e.g., the second mode described above). This will tend to reduce the value of the parameter related to leakage. For example, the switching of the valve from the first mode to the second mode may cause the parameter related to leakage to move back to (or near to) data point 36. Upon returning to (or near to) data point 36, the valve will remain in the second mode of operation.

Data point 40 is below lower threshold level 34. As such, if the parameter related to leakage proceeds from at or near data point 36 (after the valve has been switched to the second mode of operation) to data point 40, the valve is switched back to the first mode of operation. This will tend to increase the level of the parameter related to leakage. For example, switching the valve back to the first mode may cause the parameter related to leakage to move back to (or near to) data point 36.

FIG. 3 illustrates the manner in which dynamic thresholds are used to control a valve that is the same as or similar to valve 20 (shown in FIG. 1 and described above). In one embodiment, the control illustrated by the plots shown in FIG. 3 is implemented by a processor controlling the valve, such as processor 22 (shown in FIG. 1 and described above). FIG. 3 includes three plots 42, 44, and 46. The plot 42 is a plot of the parameter related to leakage versus time. The plot 44 is a plot of pressure within an interface appliance versus time. The plot 46 is a plot of the operating mode of the valve (e.g., a first, open mode, or a second, closed mode).

Depicted on the same time axis as plot 42 are an upper threshold level 48 and a lower threshold level 50 for the parameter related to leakage. As can be seen in FIG. 3, upper threshold level 48 and lower threshold level 50 depend on the pressure within the interface appliance. In particular, FIG. 3 depicts how when pressure within the interface appliance (see plot 44) drops at times D and G, respectively, upper threshold level 48 and lower threshold level 50 experience corresponding drops.

FIG. 3 also illustrates how the mode in which the valve is operating at a given time is dictated by the parameter related to leakage and threshold levels 48 and 50. Specifically, at a time A, the valve is in the first operating mode, and the level of the parameter related to leakage is between upper threshold level 48 and lower threshold level 50. At times B and F, the level of the parameter related to leakage breaches upper threshold level 48. In response, the mode of the valve is switched from the first mode to the second mode, thereby reducing leakage and lowering the level of the parameter related to leakage back in between threshold levels 48 and 50. At times E and G, the level of the parameter related to leakage breaches lower threshold level 50. This causes the mode of the valve to be switched from the second mode back to the first mode, thereby increasing leakage and increasing the level of the parameter related to leakage so that the parameter is once again between threshold levels 48 and 50.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to deliver a pressurized flow of breathable gas to the airway of a subject, the system comprising:
   a gas circuit forming an inlet, an outlet, and a lumen that places the inlet in communication with the outlet, wherein the outlet is configured to deliver the pressurized flow of breathable gas to the airway of a subject;
   a valve configured to release gas inside the circuit to atmosphere;
   one or more sensors configured to generate one or more output signals that convey information related to one or more gas parameters within the gas circuit related to gas leakage from within the circuit to atmosphere; and
   a processor configured to:
      communicate an electronic signal to the valve that controls the valve incrementally adjust a size of an opening through the valve to permit release of gas through the valve at a plurality of rates such that the amount of gas released from inside the circuit to atmosphere is based on the one or more output signals generated by the one or more sensors;
      determine an upper leak threshold based on the one or more output signals, wherein the processor is configured to control the valve such that a flow of gas released from inside the circuit through the valve is reduced or stopped if the one or more output signals generated by the one or more sensors indicate that gas leakage from within the circuit to atmosphere has risen above the determined upper leak threshold;
      adjust the upper leak threshold during inspiration and/or expiration of the subject during an individual therapy session as a function of one or more gas parameters of gas within the circuit;
   determine a lower leak threshold based on the one or more output signals, the lower leak threshold being different than the upper leak threshold, wherein the processor is configured to control the valve such that a flow of gas released from inside the circuit through the valve is increased if the one or more output signals generated by the one or more sensors indicate that gas leakage from within the circuit to atmosphere has dropped below the determined lower leak threshold, and adjust the lower leak threshold during inspiration and/or expiration of the subject during an individual therapy session as a function of the one or more gas parameters of gas within the circuit.

2. The system of claim 1, wherein the circuit comprises:
a subject interface appliance that forms the outlet of the circuit; and
a conduit that forms at least a portion of the lumen between the inlet and the outlet, the conduit being connected to the subject interface appliance,
wherein the valve is disposed on the subject interface appliance.

3. The system of claim 1, wherein the one or more output signals of the one or more sensors convey information related to a flow rate, a composition, a volume, a temperature, or humidity one within the circuit.

4. A method of delivering a pressurized flow of breathable gas to the airway of a subject, the method comprising:
delivering a pressurized flow of breathable gas to the airway of a subject through a circuit that interfaces with the airway of the subject;
generating one or more output signals that convey information related to one or more gas parameters of the pressurized flow of breathable gas related to leakage of gas in the pressurized flow of breathable gas from within the circuit to atmosphere wherein the one or more gas parameters include a flow rate, a composition, a volume, a temperature, or humidity;
determining a upper leak threshold based on the one or more output signals;
communicating an electronic signal to a valve that controls the valve incrementally adjust a size of an opening through the valve to permit release of gas within the circuit to atmosphere at a plurality of rates based on the one or more output signals generated by the one or more sensors; wherein release of gas within the circuit to atmosphere at the plurality of rates comprises reducing the rate at which gas within the circuit is released if the one or more output signals indicate that gas leakage from within the circuit to atmosphere has risen above the upper leak threshold;
adjusting the upper leak threshold during inspiration and/or expiration of the subject during an individual therapy session as a function of one or more gas parameters of gas within the circuit:
determining a lower leak threshold based on the one or more output signals, the lower leak threshold being different than the upper leak threshold;
increasing the rate at which gas within the circuit is released if the one or more output signals indicate that gas leakage from within the circuit to atmosphere has dropped below the lower leak threshold, and
adjusting the lower leak threshold during inspiration and/or expiration of the subject during an individual therapy session as a function of the one or more gas parameters of gas within the circuit.

5. The method of claim 4, wherein the circuit comprises:
a subject interface appliance that interfaces with the airway of the subject; and
a conduit that delivers the pressurized flow of breathable gas to the subject interface appliance,
wherein the gas is released from within the circuit to atmosphere at the plurality of rates through the valve, the valve disposed on the subject interface appliance.

6. The method of claim 4, wherein the one or more output signals convey information related to a flow rate, a composition, a volume, a temperature, or humidity.

7. A system configured to deliver a pressurized flow of breathable gas to the airway of a subject, the system comprising:
means for delivering a pressurized flow of breathable gas to the airway of a subject, wherein the means for delivering interfaces with the airway of the subject;
means for generating one or more output signals that convey information related to one or more gas parameters of the pressurized flow of breathable gas related to leakage of gas in the pressurized flow of breathable gas from within the means for delivering to atmosphere wherein the one or more gas parameters include a flow rate, a composition, a volume, a temperature, or humidity;
means for determining a upper leak threshold based on the one or more output signals;
means for communicating an electronic signal to means for releasing gas that controls the means for releasing gas to incrementally adjust a size of an opening through the means for releasing gas to permit release of gas within the means for delivering to atmosphere at a plurality of rates based on the one or more output signals generated by the means for generating; wherein the means for releasing gas comprises means for reducing the rate at which gas within the means for delivering is released if the one or more output signals generated by the means for generating indicate that gas leakage from within the means for delivering to atmosphere has risen above the upper leak threshold;
means for adjusting the upper leak threshold during inspiration and/or expiration of the subject during an individual therapy session as a function of one or more gas parameters of gas within the means for delivering;
means for determining a lower leak threshold based on the one or more output signals, the lower leak threshold being different than the upper leak threshold;
means for increasing the rate at which gas within the means for delivering is released if the one or more output signals generated by the means for generating indicate that gas leakage from within the means for delivering to atmosphere has dropped below the lower leak threshold; and
means for adjusting the lower leak threshold during inspiration and/or expiration of the subject during an individual therapy session as a function of the one or more gas parameters of gas within the means for delivering.

8. The system of claim 7, wherein the means for delivering comprises:
a subject interface appliance that interfaces with the airway of the subject; and
a conduit that delivers the pressurized flow of breathable gas to the subject interface appliance,
wherein the means for releasing comprises a valve disposed on the subject interface appliance.

9. The system of claim 7, wherein the one or more output signals convey information related to a flow rate, a composition, a volume, a temperature, or humidity within the means for delivering.

* * * * *